US011144116B2

(12) United States Patent
Malafeew

(10) Patent No.: US 11,144,116 B2
(45) Date of Patent: Oct. 12, 2021

(54) VIRTUAL REALITY EXERCISE GAME

(71) Applicant: Virzoom, Inc., Cambridge, MA (US)

(72) Inventor: Eric Malafeew, Lexington, MA (US)

(73) Assignee: Virzoom, Inc., Cambridge, MA (US)

( * ) Notice: Subject to any disclaimer, the term of this patent is extended or adjusted under 35 U.S.C. 154(b) by 0 days.

(21) Appl. No.: 16/449,658

(22) Filed: Jun. 24, 2019

(65) Prior Publication Data

US 2020/0150756 A1 May 14, 2020

Related U.S. Application Data

(63) Continuation of application No. 15/086,773, filed on Mar. 31, 2016, now Pat. No. 10,379,604.
(Continued)

(51) Int. Cl.
*G09G 5/00* (2006.01)
*G06F 3/01* (2006.01)
(Continued)

(52) U.S. Cl.
CPC .............. *G06F 3/012* (2013.01); *A63B 69/16* (2013.01); *A63B 71/0622* (2013.01);
(Continued)

(58) Field of Classification Search
CPC ............. G06F 3/04845; G06F 3/04855; G06F 17/212; G06T 11/60; G06T 11/206
(Continued)

(56) References Cited

U.S. PATENT DOCUMENTS 5,577,981 A    11/1996   Jarvik
5,762,612 A *   6/1998   Campbell ............... G06F 3/011
                                                                                                                600/558
(Continued)

FOREIGN PATENT DOCUMENTS

JP       H04 061869       2/1992
JP       H09 081024       3/1997
(Continued)

OTHER PUBLICATIONS

EP Supplemental European Search Report in International Appln. 16777070, dated Feb. 13, 2019, 12 pages.
(Continued)

*Primary Examiner* — Gordon G Liu
(74) *Attorney, Agent, or Firm* — Fish & Richardson P.C.

(57) ABSTRACT

Methods, systems, and apparatus, including computer programs encoded on computer storage media, for a virtual reality exercise game. One of the methods includes determining a head rotation of the user and a head lean of the user on an exercise device based on data from one or more sensors. The method includes presenting a virtual reality environment on a virtual reality headset, wherein the perspective of the user in the virtual world is determined by a vehicle that defines the velocity of the perspective, a body which defines a reference view point of the perspective (with the head looking forward), and a head which defines the view point of the perspective. The method also includes determining to apply rotation to the body in response to determining that a direction of the head rotation is in a direction of the lean.

16 Claims, 8 Drawing Sheets

Related U.S. Application Data

(60) Provisional application No. 62/146,126, filed on Apr. 10, 2015.

(51) Int. Cl.
| | | |
|---|---|---|
| *A63B 69/16* | (2006.01) | |
| *A63B 71/06* | (2006.01) | |
| *A63F 13/245* | (2014.01) | |
| *A63F 13/525* | (2014.01) | |
| *G16H 20/30* | (2018.01) | |
| *A63B 69/00* | (2006.01) | |
| *A63B 22/00* | (2006.01) | |
| *A63B 22/06* | (2006.01) | |
| *H04M 1/72412* | (2021.01) | |

(52) U.S. Cl.
CPC .......... *A63F 13/245* (2014.09); *A63F 13/525* (2014.09); *G16H 20/30* (2018.01); *A63B 22/0076* (2013.01); *A63B 22/0605* (2013.01); *A63B 69/0093* (2013.01); *A63B 2071/0625* (2013.01); *A63B 2071/0638* (2013.01); *A63B 2071/0644* (2013.01); *A63B 2071/0666* (2013.01); *A63B 2220/10* (2013.01); *A63B 2220/17* (2013.01); *A63B 2220/30* (2013.01); *A63B 2220/803* (2013.01); *A63B 2220/836* (2013.01); *A63B 2225/02* (2013.01); *A63B 2225/20* (2013.01); *A63B 2225/50* (2013.01); *H04M 1/72412* (2021.01)

(58) Field of Classification Search
USPC .......................................................... 345/633
See application file for complete search history.

(56) References Cited

U.S. PATENT DOCUMENTS

| | | |
|---|---|---|
| 6,351,261 B1 | 2/2002 | Reichlen et al. |
| 2007/0072662 A1* | 3/2007 | Templeman ............ A63F 13/00 463/6 |
| 2009/0011907 A1* | 1/2009 | Radow ............... A63B 24/0084 482/57 |
| 2010/0022354 A1 | 1/2010 | Fisher |
| 2010/0035726 A1 | 2/2010 | Fisher et al. |
| 2013/0278631 A1 | 10/2013 | Border et al. |
| 2014/0176296 A1 | 6/2014 | Morgan |
| 2014/0243156 A1 | 8/2014 | Cohen |

FOREIGN PATENT DOCUMENTS

| | | |
|---|---|---|
| JP | H11 347249 | 12/1999 |
| JP | 2002525769 | 8/2002 |
| JP | 2007331426 | 12/2007 |
| JP | 2010091955 | 4/2010 |
| JP | 2012042881 | 3/2012 |
| WO | WO 2013/168171 | 11/2013 |
| WO | WO 2014/084742 | 6/2014 |

OTHER PUBLICATIONS

PCT International Preliminary Report on Patentability in International Appln. PCT/US2016/025172, dated Oct. 10, 2017, 9 pages.

PCT International Search Report and Written Opinion in International Appln. PCT/US16/25172, dated Aug. 22, 2016, 15 pages.

PCT Invitation to Pay Fees in International Appln PCT/US2016/025172, dated Jun. 13, 2016, 2 pages.

Swedberg [online], "Safer Ski Jumps: Design of Landing Surfaces and Clothoidal In-run Transition," Jun. 2010, [retrieved on Jun. 29, 2017] Retrieved from URL <http://www.dtic.mil/dtic/tr/fulltext/u2/a524748.pdf>.

YouTube.com [online], "Virtual Reality Mountain Biking with Oculus Rift," Feb. 13, 2015, retrieved from URL <https://www.voutube.eornlwatehN=PDb2zoxSZa> [retrieved Apr. 19, 2019], 2 pages.

YouTube.com [online], The World's Most Awesome Bike Simulator, retrieved from URL <https://www.youtube.comlwatch?v—rixSpWZjii3eg> [retrieved Apr. 19, 2019], 2 pages.

\* cited by examiner

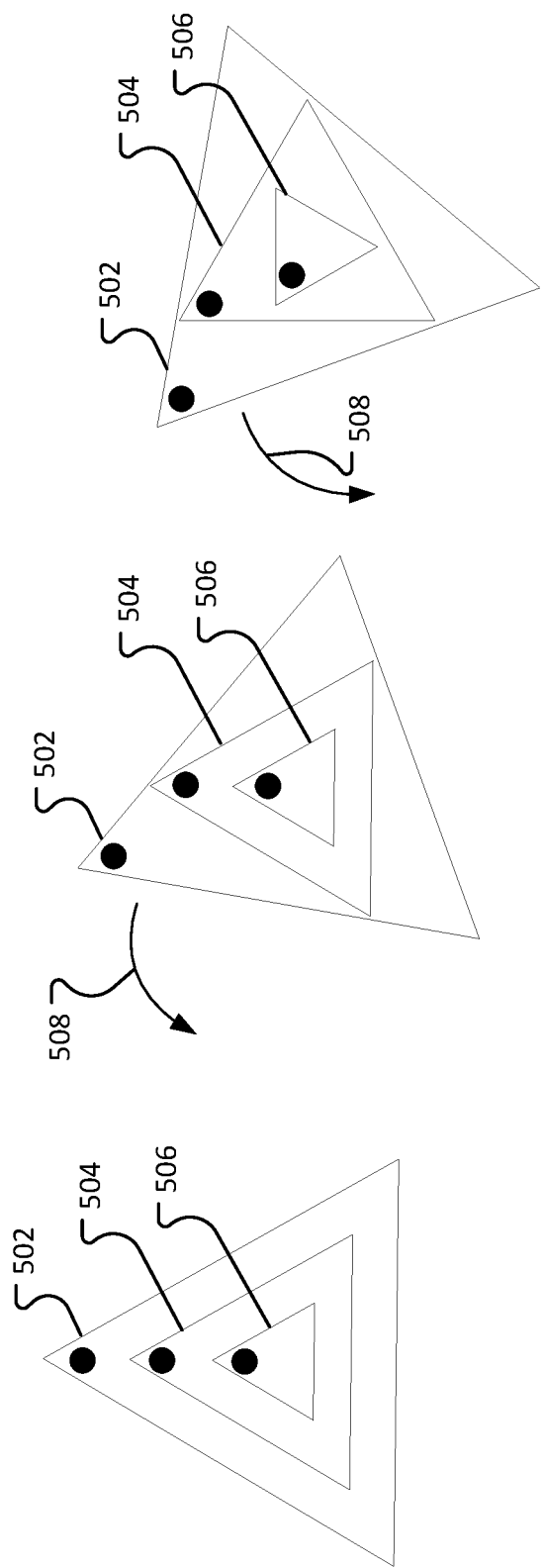

VIRTUAL REALITY EXERCISE GAME

CLAIM OF PRIORITY

This application is a continuation application to U.S. patent application Ser. No. 15/086,773, filed on Mar. 31, 2016, which claims priority under 35 USC § 119(e) to U.S. Patent Application Ser. No. 62/146,126, entitled "Virtual Reality Exercise Game", filed on Apr. 10, 2015, the entire contents of which are hereby incorporated by reference.

BACKGROUND

Physical exercise is any bodily activity that enhances or maintains physical fitness and overall health and wellness. It is performed for various reasons, including strengthening muscles and the cardiovascular system, honing athletic skills, and weight loss or maintenance. The U.S. Center of Disease Control and Prevention recommends that adults get about four hours of physical activity each week. Americans, on average, fall short of these recommendations.

SUMMARY

This specification describes technologies relating to virtual reality and exercise equipment.

In general, the innovative aspects of the subject matter described in this specification can be embodied in a system that includes an exercise device. The system also includes one or more processors configured to determine whether to rotate a reference view point of a virtual reality environment displayed on a virtual reality headset based on a steering input and a head rotation input from the user on the exercise device, comprising determining to rotate the reference view point if the steering input indicates a turn and the head rotation input indicates that the user is looking into the turn.

In general, other innovative aspects of the subject matter described in this specification can be embodied in a system that includes an exercise device. The system also includes one or more processors configured to determine a head rotation of the user and a head lean of the user on the exercise device based on data from one or more sensors. The sensors are also configured to present a virtual reality environment on a virtual reality headset, wherein the perspective of the user in the virtual world is determined by a vehicle that defines the velocity of the perspective, a body which defines a reference view point of the perspective (with the head looking forward), and a head which defines the view point of the perspective. The processor is also configured to determine to apply rotation to the body in response to determining that a direction of the head rotation is the toward a direction of the lean.

Other embodiments of this aspect include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

Particular embodiments of the subject matter described in this specification can be implemented so as to realize one or more of the following advantages. Physical activity on an exercise device can be translated into intuitive motions in a virtual world. An engaging three to four minute exercise loop can be created. Users can be incentivized to exercise. Exercise activities can be more enjoyable. Queasiness associated with virtual reality can be reduced.

The embodiments may include one or more of the following features, alone or in combination. Determining whether to rotate the reference view point further may include determining to not to rotate the reference view point if the steering input indicates a turn and the head rotation input indicates that the user is not looking into the turn. A magnitude of the rotation of the reference view point may be determined based on the steering input and the head rotation input. The exercise device may be coupled to one or more sensor configured to detect a speed input and the magnitude of the rotation of the reference view point may be further determined based on the speed input. The processor may be configured to determine the steering input from a head position input, in the left/right direction from a default centered position, including compensating for the natural movement of a user's head while using the exercise device and looking around. The head tracking inputs may be associated with the virtual reality headset. The steering input may determine a relative direction of a velocity of the vehicle to a direction of the body. The embodiments may include translating a pedaling velocity into a virtual velocity that is modulated by a virtual slope of a virtual terrain, such that the virtual velocity is decreased when the virtual slope is uphill and increased when the virtual slope is downhill. The embodiments may include softening landings on virtual terrain from virtual flight or virtual falls, by limiting the downward velocity in proportion to the height above the terrain. The virtual body may not pitch or roll, thereby keeping the sense of gravity of the user the same between virtual view point of the user and vestibular (inner ear) system.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIG. 5A-E illustrate examples of the responses of the vehicle and body to a steering input and head rotation.

Like reference numbers and designations in the various drawings indicate like elements.

DETAILED DESCRIPTION

Sensors may be attached to an exercise device and integrated into a virtual reality system. Data provided by the sensor can enable the user to explore virtual reality environments. Examples of different virtual reality environments that a user may explore include, but are not limited to, a horse traveling along a winding and hilly canyon road, a bee flitting between flowers, a tank competing with other tanks on a battlefield, a dragon engaged in combat against knights and wizards, a surfer paddling his surfboard out in search on waves, a dinosaurs hunting for prey, an airplane flying through the sky, and a spaceship exploring the galaxy in search of new planets. Each of these experiences integrates entertainment with the otherwise mundane task of exercising.

Exercise machines are well suited as virtual reality controls because they are simulators of motion. An exercise bike simulates riding a bicycle. A rowing machine simulates rowing a boat, etc. . . . . Furthermore, because exercise machines are stationary, they are safe to operate when the user's eyes are covered, for example, by a virtual reality headset.

Because the virtual reality system is largely controlled by data received from the sensors, the system requires minimal additional inputs. For example, a simple button control (for example, pressed by the thumb) may be sufficient to enable the user to perform most tasks.

Many people experience a sense of illness or unease when wearing a virtual reality headset; this unease is sometimes referred to as simulation sickness. Simulation sickness is a form of visually induced motion sickness. Simulation sickness can have many causes. For example, simulation sickness can be caused by a low refresh rate of an on-screen image, a lag between when an action is taken and when the action appears in the virtual reality environment, and a disparity between the apparent motion provided by the visual and vestibular stimuli.

Improvements in the hardware and software used in virtual reality headsets can address simulation sickness due to refresh rate and lag. The virtual reality system described below can reduce or eliminate the simulation sickness caused by the disparity in stimuli from the visual and vestibular system.

While the virtual reality worlds consist of a series of images projected onto a stereoscopic display and the user is not required to physically relocate when navigating through the virtual reality environment, for simplicity, changes in perspective which simulate motion through the virtual reality environment will be described in terms of motion.

Physical Setup and Sensors

Figure 1:
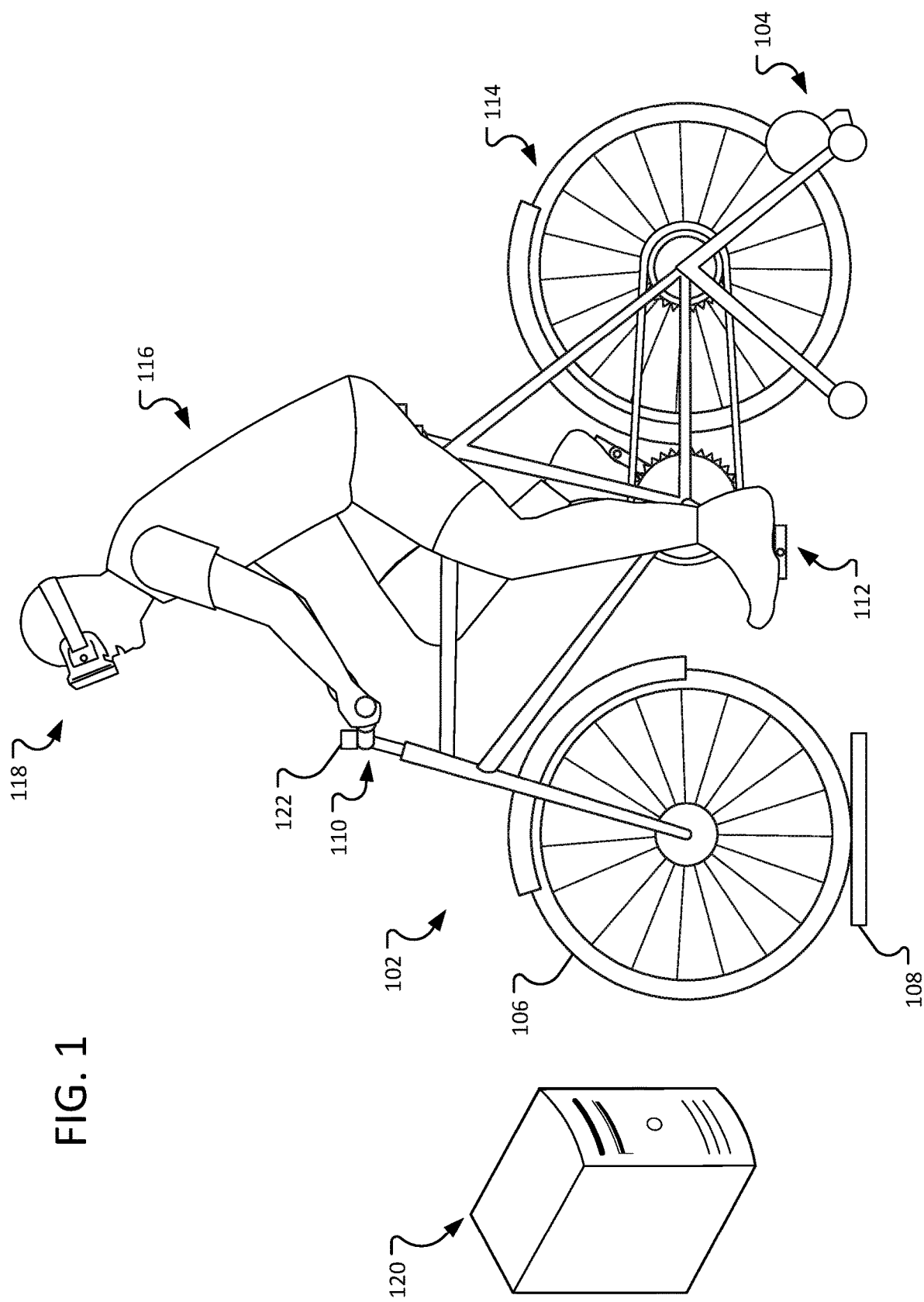
FIG. 1 illustrates an example of a virtual reality exercise system.

FIG. 1 illustrates an example of a virtual reality exercise system. In this example, a bicycle 102 is placed on a resistance trainer 104, or other similar device. In general, a resistance trainer is a device that enables a standard bicycle to function as a stationary bicycle. The front wheel 106 of the bicycle rests on a turn table 108. Turning the handlebars 112 causes the turn table 108 to rotate around an axis. The turn table 108 allows the handlebars of the bicycle to turn without jarring the bicycle 102. Some sensors can measure the angular rotation of the handlebars 110 and/or the front wheel 106 (rotation of the handle bars causes rotation of the wheel). Some sensors can measure the rotations of the pedal assembly 112 or the rear wheel 114. In this example, a rotation of the pedal assembly 112 causes one or more rotations of the rear wheel 114.

The rotation of the handle bars and/or wheel can be detected, for example, by potentiometer or other sensor capable of detecting rotation or measuring the angle of rotation. Sensor used to detect the rotation of the handlebars 112 and/or front wheel 106 is referred to herein as steering sensors. The steering sensors can measure the magnitude and direction of the rotation. In some implementations, the signal from a steering sensor is sufficient to determine the angle of the wheel and/or handle bars. In some implementations, a steering sensor can be coupled to the turn table 108. In some implementations, a steering sensor can be coupled to the handlebars (for example, the rotational sensor may be coupled to the steerer tube or handlebars of the bicycle). The sensors may be coupled to the bicycle so that the sensors do not need to be removed during normal operation (for example, if the user removes the bicycle 102 from the trainer 104 and uses it outside).

Other steering devices and steering sensors can be used. For example, a steering device could include a joystick, control pad (for example, a game pad or a d-pad), or other similar device. The steering sensor could be embedded in the device and may send data indicative of movement controls executed by the user.

The rotations of the pedal assembly 112 or rear wheel 114 can be measured by an accelerometer. The rotation of the pedal assembly 112 or rear wheel 114 can also be measured by a photoelectric sensor that detects rotations of the wheel or pedal assembly (for example, by counting marks placed on the rear tire). Rotation of the pedal assembly or rear wheel can also be measured by attached magnets passing by one or more magnetic sensors, such as a reed switch or "hall effect" sensor. As used herein, the sensor used to detect rotations of the pedal assembly or rear tire is referred to as the speed sensors.

In some implementations, a user activated control 110 is coupled to the handle bars 110. The user activated control may be, for example, a button, switch, control pad, or other device. The user activated control may also include multiple buttons, switches, or other controls. The user activated control may be placed so that the user may reach the user activated control without removing their hands from the handlebars 110. A sensor integrated into the user activated control can determine that the user has operated the user activated control 110. In some implementations, data from the user activated control may be used as a steering input.

A user 116 rides the bicycle 102 while wearing a virtual reality headset 118, or similar device. The virtual reality headset 118 delivers visual and/or audio stimulation to the user. Virtual reality generally refers to a computer-simulated environment that can simulate physical presence in places in the real world or imagined worlds. The virtual reality headset can include stereoscopic displays that present a virtual reality to the user.

The virtual reality headset may include sensors that can detect motion of the headset, including forward/backward motion, left/right motion, up/down motion, pitch, roll, and yaw. Sensors that detect the motion of the head of the user are referred to, generally, as head sensors.

The head sensor can include head position sensors that detect forward/backward, left/right, and up/down motion of the headset. The head sensors can also include head rotation sensors that detect pitch, yaw, and roll of the headset. In some implementations, the head position sensors and the head rotation sensors can be the same sensors.

Data provided by the sensors can be provided to a computer system 120. The sensors may connect to the computer system 120 either through either wireless or wired connections or both. For example, the steering sensor, speed sensor, and user control may provide data to the computer system 120 through a wireless connection (for example, a BLUETOOTH connection). The virtual reality headset may provide data to the computer system 120 through a wired connection (for example, connected to a USB port on the computer (not shown)) or communicate with a built-in computer system (for example, a VR-capable mobile phone such as the Samsung Gear VR). In some implementations, the sensor data can be encrypted prior to being delivered to the computer system 120.

A user operating exercise equipment, such as the bicycle 102 or a rowing machine (not shown) has a posture-enforced default head position. Therefore, a resting or stating position can be established which allows the data from the sensors to be used to determine changes from the default position. For example, a change in the left/right position of the head can be used to determine that the user is leaning in a particular direction.

The sensors can provide a measurement of speed, a measurement of steering (for example, a measure of turn applied to the handlebars or other steering device), a degree of head rotation (an angle of pitch, roll, and yaw from a resting forward position), a measurement of the left right position of the head (for example, if the user on the bicycle leans to the right, it will cause the sensors to indicate that the position of the head is the right). The sensors can also provide user activated control data (for example, an indication that the user has pressed a button).

In some implementations, the sensor can also provide a measure of the forward and backward position of the head.

The sensors can provide data to the computer system periodically or when the data changes. For example, the sensors may be sampled at 30 hertz. In some implementations, some or all of the data may be processed by a second order filter to smooth out any sudden changes in the data.

Figure 2:
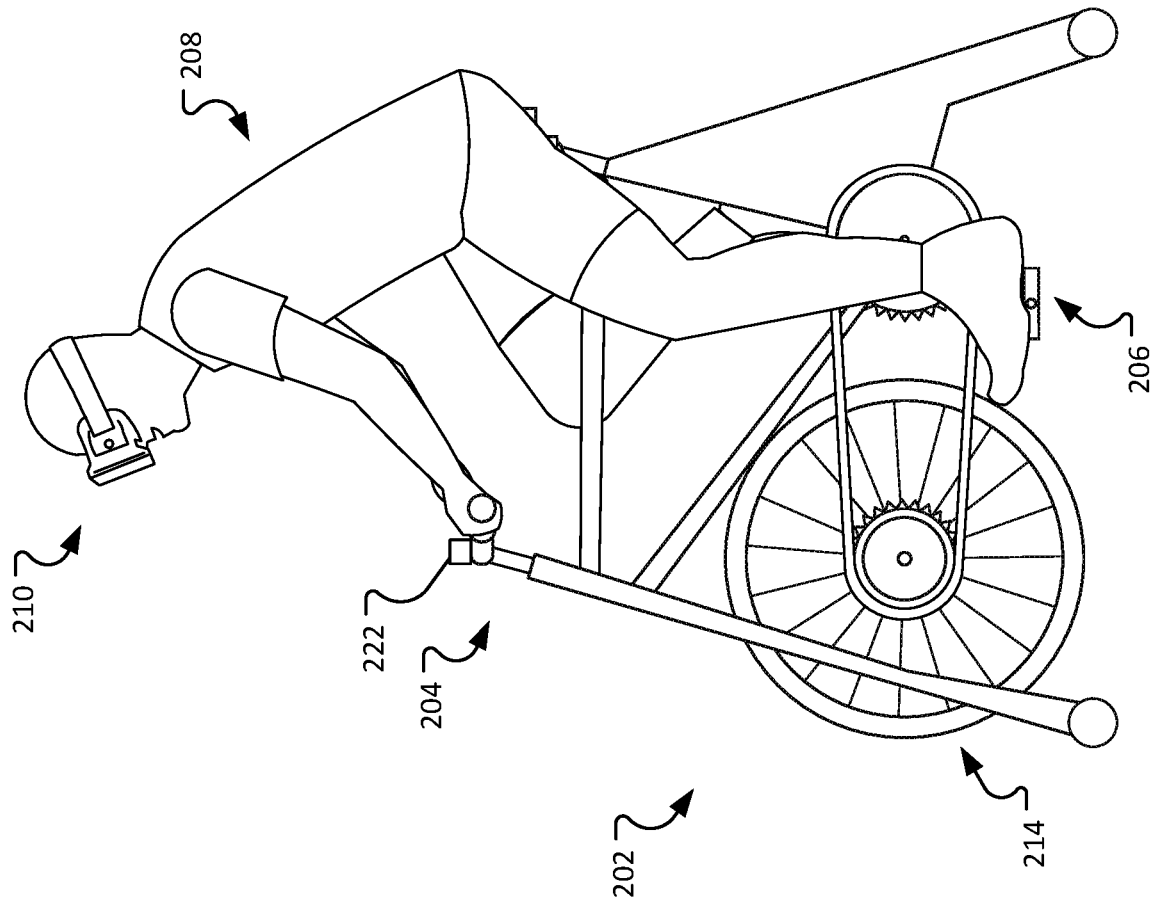
FIG. 2 illustrates another example of a virtual reality exercise system.
Figure 2:
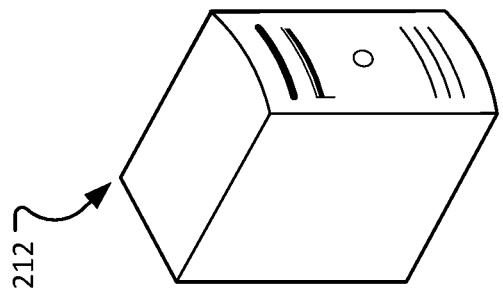

FIG. 2 illustrates another example of a virtual reality exercise system. In this example, a stationary bicycle 202 is used in conjunction with a virtual reality system.

Unlike the bicycle 102 of FIG. 1, the stationary bicycle 202 may not have moveable handlebars. In this scenario, the steering sensors may be omitted. Instead, the system may use the lean of the user as the steering input.

Alternatively or additionally, a steering input may be received from user-activated controls, for example, using a control pad or other device attached to the handlebars of the stationary bicycle. While the stationary bicycle 202 is referred to as a bicycle, it should be understood that the stationary bicycle does not need to have two wheels or any wheels. Instead, a stationary bicycle can be any piece of exercise equipment that simulates the physical experience of riding a bicycle.

Sensors on the stationary bicycle can measure rotations of the pedal assembly 206 or the drive wheel 214. In this example, a rotation of the pedal assembly 206 causes one or more rotations of the drive wheel 214. In some implementations, the stationary bicycle may not have an exposed drive wheel 214. In this scenario, the speed sensors may be attached to the pedal assembly.

The rotations of the pedal assembly 206 or drive wheel 214 (or any other wheel or device driven by the rotation of the pedal assembly 206) can be measured by a speed sensor, as described above.

In some implementations, a user activated control (not shown) is coupled to the handle bars 204. The user activated control may be, for example, a button, switch, control pad, or other device. The user activated control may also include multiple buttons, switches, control pads, or other devices. A sensor integrated into the user activated control can determine that the user has activated the user activated control.

A user 206 rides the stationary bicycle 202 while wearing a virtual reality headset 210, or similar device. As described above, the virtual reality headset may include sensor that can detect motion of the headset, including, forward/backward motion, left/right motion, up/down motion, pitch roll and yaw.

Data provided by the sensors can be provided to a computer system 212, as described above.

Interpretation of Sensor Data

The computer system can use the data from the sensors to calculate speed, lean, steering input, and the angle of head rotation.

Speed may be calculated by translating either pedal rotations or wheel rotations into a distance and then dividing the distance by the amount of time that passed since the last sampling. In implementations where the speed sensors measure rotations of the pedal assembly, the system may compensate for a stop in pedaling by applying a constant breaking deceleration.

Within the virtual environment, the direction the user travels in the virtual reality environment may be described using a vector. The velocity of the user in the virtual reality environment may be determined by multiplying a unit vector indicative of direction by the speed.

The velocity may be adjusted based on the needs of the virtual reality environment. For example, for a horse riding virtual game, the velocity may be doubled. For a horse race virtual game, the velocity may be multiplied by 2.25, etc. . . .

A head lean may be determined based on the left/right position of the head as reported by the virtual reality headset. The computer may determine that changes in position of the Virtual Reality Headset that are less than a certain threshold are not indicative of lean. For example, a change in position of equal to or less than 0.2 meters, or 20 centimeters may be ignored. The head lean can be converted into a measure of steering input. For example, the head lean can be multiplied or divided by a constant. The constant may be user configurable so that the user may set the amount of lean he prefers.

In some implementations, the calculation of lean must be adjusted based on the direction the user is looking. In general, as the user turns their head, the position of the virtual reality headset changes because it is mounted over their face. For example, if a user is looking to the right, then the left/right position of the headset will be more to the right. If the user is looking to the left, the left/right position of the headset will be more to the left. The computer system can compensate by reducing or increasing the calculation of lean based on the direction the user is looking.

An example of a computer program to compensate for the turn of the head is reproduced below, where head width is a distance from the turning axis to the virtual reality headset:

```
Head Lean = Left / Right Head Sensor Position
if (Head Rotation Angle > 90 degrees off center)
    Head Lean = Head Lean − Head Width;
else
    HeadLean = Head Lean − Head Width * sin(Head Rotation Angle);
```

In some implementations, to determine steering behavior, the system can accept multiple different inputs. For example, a user may indicate steering by rotating the handle bars of a bicycle. The user may also indicate steering by operating a direction control on a keyboard or other game controller. The user may also indicate steering by leaning to one side of the bicycle. A lean can be detected based on left/right movement of the virtual reality headset worn by the user.

If the system receives multiple steering inputs that each indicate steering in the same direction, the direction and size of steering can be determined based on the largest steering metric. For example if a user both rotates the handlebars to the right and leans to the right the magnitude of steering can be determined based on whichever input results in greater steering to the right. Similarly, if the user both rotates the handlebars to the left and leans to the left, the magnitude of steering can be determined by whichever input results in greater steering to the left. However, if the system receives multiple steering inputs where each input indicates steering in a different direction, the magnitude of steering can be determined by adding the turn inputs. For example, if the user rotates the handlebars to the right a small amount and leans to the left a greater amount, then the system can determine to steer slightly to the left. Similarly, if the user rotates the handlebars to the right a large amount and leans to left a smaller amount, then the system will determine to steer slightly to the right.

In some implementations, steering to the left may be indicated by data that includes a number that is less than zero and steering to the right may be indicated by data that includes a number that is greater than zero. In such implementations, the following is an example of pseudo-code that could be used to perform the operation:

```
if (handlebars and lean are in the same direction)
{
    if (both to the right)
        return maximum of handlebars and lean
    else
        return minimum of handlebars and lean
}
else
    return sum of handlebars and lean
}
```

The steering input can be used by the system to cause changes in the perspective of the virtual environment.

In some implementations, the forward/backward head position can be used to control the pitch of a vehicle. For example, leaning forward may cause a virtual airplane to dive, while leaning backward may cause the virtual airplane to climb.

Calibration

In some implementations, the computer system may prompt the user to configure the sensors when an exercise or gaming session begins. For example, when the user puts on the virtual reality headset, they may receive a prompt request that they look forward and begin pedaling. Once the user begins pedaling at a predetermined rate (for example, a number of revolutions per minute) for a predetermined period of time (for example a number of seconds) the system may calibrate the system based on the data from the sensors. The user may also hold down one or more buttons when so prompted to calibrate the sensors.

In some implementations, the system may request that the user pedal at the equivalent of 2-3 miles per hour for 1-2 seconds. As the bicycle is stationary, the miles per hour of speed of the bicycle may be determined based on the rate at which the user is pedaling the bicycle, the rate at which the rear or drive tire is moving, etc. . . . .

The calibration process may include, for example, determining an initial direction of a virtual vehicle and body in the virtual reality environment, determining an initial orientation and position of the user's head corresponding to the direction that the user views as forward, and the steering data that corresponds to a forward direction.

Once calibrated, the system can accept data from the sensors to determine positional velocity and rotational or angular velocity (turning). As described above, velocity can be determined based on the number of rotations of the pedal assembly or the drive tire.

Movement in Virtual Reality

Figure 3:
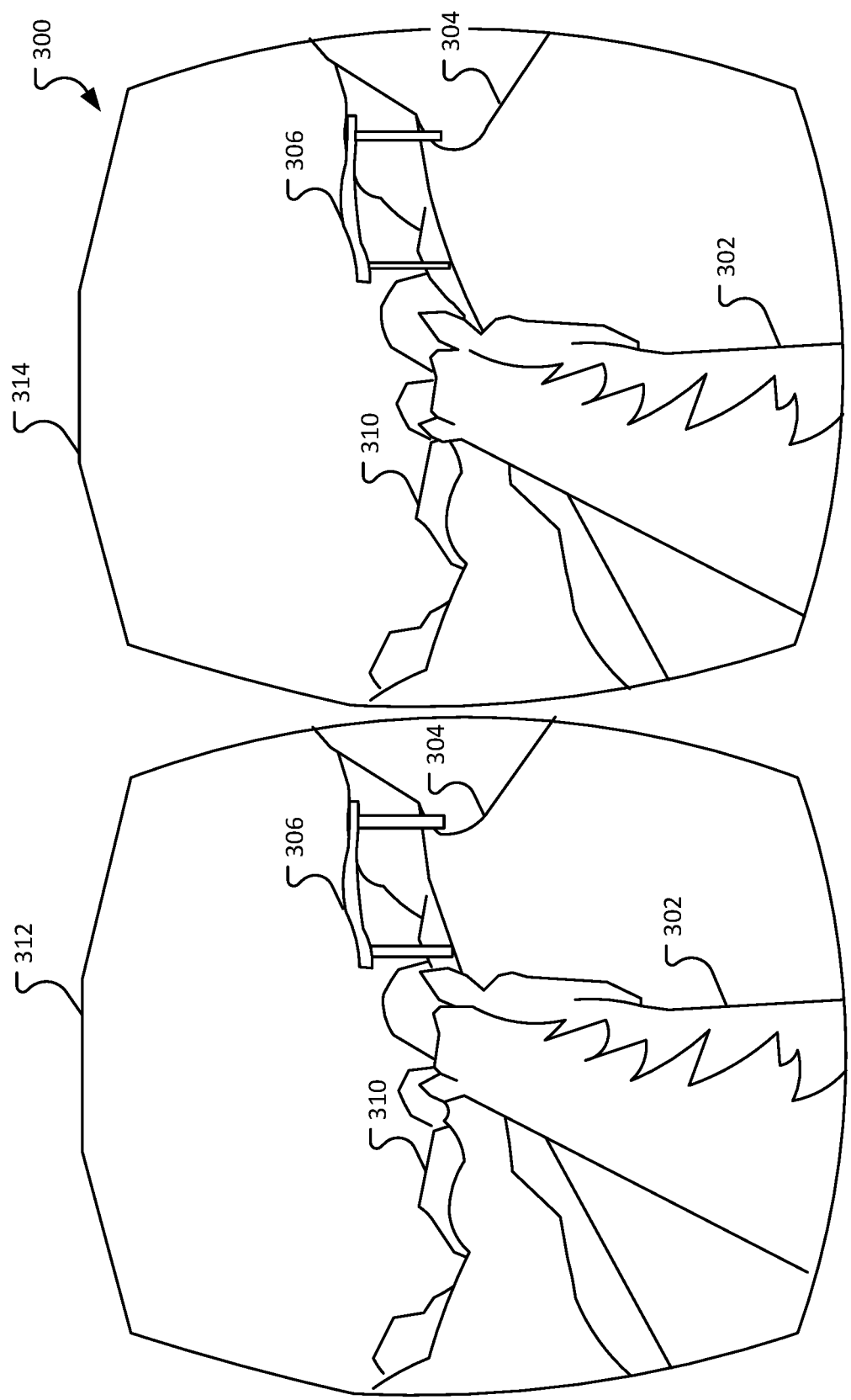
FIG. 3 illustrates an example of a game displayed on stereoscopic screens 300 to a user as part of a virtual reality environment.

FIG. 3 illustrates an example of a game displayed on stereoscopic screens 300 to a user as part of a virtual reality environment. The virtual reality environment can be generated and controlled by a computer system (for example, a personal computer). Graphics or images to be presented to the user can be created using specialized hardware, such as a graphics card. The graphics can be delivered to the user through a headset that contains two monitors, one for each eye (for example monitors 312, 314). Each monitor shows a slightly different image projection of the same three-dimensional model. The images create a stereoscopic effect, giving the illusion of depth. In general, the stereoscopic display in virtual reality mimics the stereoscopic vision of the user, therefore, the image displayed in each monitor is slightly offset (for example, by about 65 mm).

The user provides input (for example, by pedaling, looking around, leaning, or turning the bicycle) which the computer system translates into a velocity and rotational velocity. These inputs are used to navigate the user through the three dimensional model. Motion throughout the virtual environment changes the location of a projection plane, and accordingly, the image projected onto the monitors.

Projection refers to any method of mapping three-dimensional points onto a two-dimensional plane. As most current methods for displaying graphical data are based on two-dimensional screens, the use of this type of projection is widespread, especially in computer graphics, engineering and drafting. For stereoscopic views, the projection can be performed twice, once for the image presented to the left eye and once for the image presented to the right eye.

The displays 300 illustrate a stereoscopic image of a three dimensional landscape. In this example, the landscape includes a path 304 that wanders through a valley. In this example, the user is not visible, however, a horse 302 is partially visible. The image of the horse 302 is constructed to give the user the visual sense that the user is riding the horse 302.

In the background of the valley there can be trees and other environmental items. The horse may not be constrained to travel along the path 304 but may be free to navigate in any direction through the virtual environment. The user may "ride" the horse through the virtual environment. The environment may include hills and valleys.

Along the path 304 there may be gates 306 which the user is encouraged to pass through. For example, the system may tally the number of gates skipped.

Figure 4:
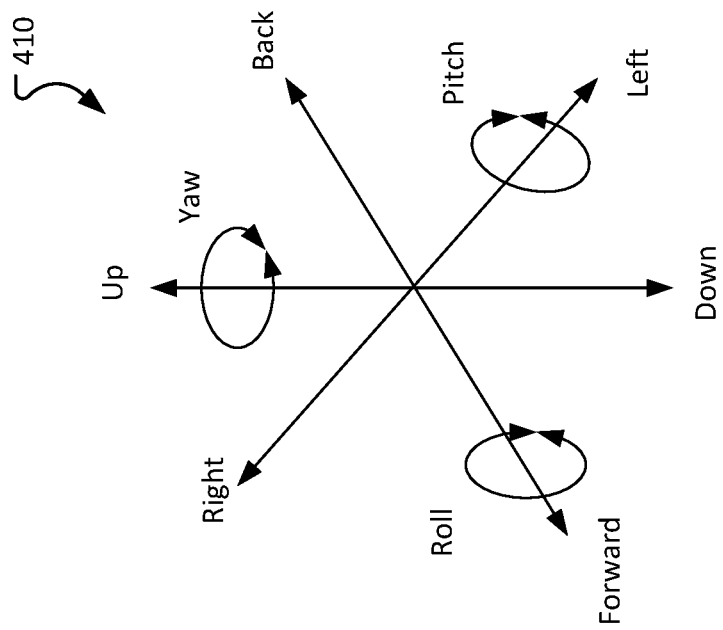
FIG. 4 illustrates an example of a virtual body that dictates changes in perspective in the virtual environment.
Figure 4:
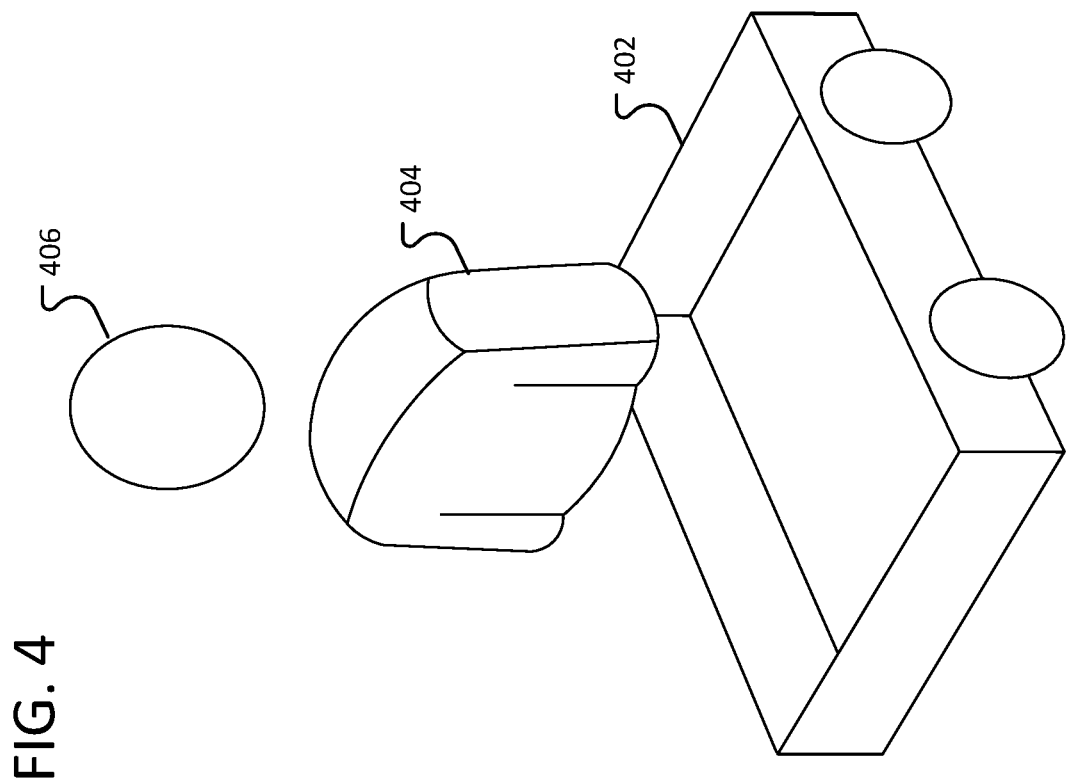

FIG. 4 illustrates an example of a virtual rig comprised of an interconnected vehicle, body, and head that dictates changes in perspective in the virtual environment. A conceptual vehicle 402 is used to traverse the virtual environment. For clarity, the guide 410 illustrates the range of motion in the virtual space. For example, the guide 410 shows forward, back, right, left, up, down, roll, pitch, and yaw. These movements may be combined in any order to traverse through the virtual environment.

The vehicle 402 determines the direction and velocity of movement through the environment. The vehicle may move in any direction, forward/backward, up/down, left/right, pitch, roll, or yaw. Generally the vehicle is oriented in the direction of its velocity. The movement of the vehicle 402 may be constrained based on the geometry of the virtual environment (e.g., the ground, trees, and other objects in the geometry) or the vehicle may be able to navigate independent of such constraints (e.g., fly, clip through the ground, trees, etc.), although, generally speaking, some users may find clipping and diving through the ground to be uncomfortable. The vehicle may or may not be represented in the virtual environment. Returning to FIG. 3, the vehicle is represented by the horse 302.

Returning to FIG. 4, a body 404 can be positioned on the vehicle. The body motion in the forward/backward, up/down, and right/left directions is inherited from the vehicle. However, the yaw motion of the body may be determined independently of the vehicle, and determine the yaw of the vehicle and its direction of travel. In most implementations, the body does not roll or pitch. In general, for many applications applying a roll or pitch to the virtual body can disorient the user because the user, generally, expects gravity to be pulling down. A change in pitch or roll alters the gravity so the effect of gravity on the virtual body is different from the effect of gravity on the user's actual body. This difference between the actual pull of gravity on the user and the apparent pull of gravity in the virtual reality environment can cause disorientation and discomfort.

The body may or may not be represented in the virtual environment. For example, in FIG. 3, the body is not graphically rendered. The body determines a reference view point of a facing direction, or a direction the user faces when the head 406 is faced forward.

A head 406 is positioned directly above or below the body 404. The motion of the head inherits the position and rotation of the body 404, and is additionally moved and rotated to follow the user's actual head as determined by the virtual reality head sensors. The rotational angle the head 406 faces in at rest (e.g., when the user of the virtual reality device is looking directly ahead) is aligned with the rotational angle of the virtual body 404.

Some users may experience simulation sickness which can occur when exposure to a virtual environment causes symptoms similar to those of motion sickness. For example a user may experience queasiness, nausea, sweating, disorientation, etc. Simulation sickness may be caused by sensory conflict (for example, the inner ear suggests the user is not moving but visual input suggests that the user is moving). Simulation sickness may be reduced by using a combination of data from the steering sensors and head sensors as described more below.

Data provided from the steering sensors may indicate that the user wishes to turn. For example the steering input may indicate that the vehicle 402 should yaw (rotate about the up/down axis) to head in a new direction. The yaw may be accompanied by movement in the forward/back direction. If the virtual reality system causes the virtual head to rotate much differently than the user's actual head, the user may experience discomfort. Because the head rotates along with the body, this can also be caused by the turning of the virtual body in a way that is not correlated with the user's vestibular senses.

Instead, the virtual reality system can use additional data from the head sensors to determine whether the body 404 should yaw when the vehicle is turning. For example, if the data from a head sensor indicates that the user is looking into the turn (that is, the user is looking in the direction of the turn) then the body 404 yaws along with the vehicle, however, if the data from the head sensor indicates that the user is not looking into the turn (that is, the user is looking straight ahead or in a different direction) then the body 404 does not yaw along with the vehicle. The body would instead maintain its angular position relative to a reference direction. A maximum turn relative to the body can be enforced. For example, the vehicle may be limited to a maximum turn of thirty degrees off center (from the resting position of the head).

In scenarios where the system determines to turn (yaw) the body, the magnitude of the turn can be limited based on the vehicle angle of rotation, the steering input, and the head angle of rotation (yaw). In one implementation the magnitude of the turn can be determined by the head rotation so long as the head rotation does not exceed the vehicle rotation (or the lesser of the head rotation and vehicle rotation). In some implementation, the amount of yaw imparted to the body is proportional to the amount the user is looking into the turn, up to the amount of the turn input. Therefore absent steering input, the user can freely turn their head to look around the virtual landscape without applying yaw to the body.

Example pseudo-code to perform a turning operation is provided below:

```
if (Head Angle of Rotation >= 0 && Vehicle Angle of Rotation <= 0)
    Body rotational velocity = 0;
else if (Head Angle of Rotation <= 0 && Vehicle Angle of Rotation >= 0)
    Body rotational velocity = 0;
else if (Head Rotation > 0)
    Body rotational velocity = Clamp(Head Rot, 0, Vehicle Rotation);
else
    Body rotational velocity = Clamp(HeadRot, Vehicle Rotation, 0);
```

The turning operation above can reduce discomfort associated with simulation sickness because the algorithm can induce the user to rotate their head to initiate rotational velocity of the virtual body (up to the limit of the steering input) by preventing the virtual body from rotating with the steering input when the user is not looking in the direction of the turn. Absent looking into the turn, the steering input is translated into vehicle rotation, which affects the velocity direction but does not change the rotational perspective of the user.

For example, in the scenario where the vehicle has a forward velocity with the user initially looking straight forward with a centered steering input. The user then indicates steering to one side, for example, by leaning in the left/right direction. If the user does not also turn his head, the virtual motion is similar to changing lands on a highway. When the steering input is recentered (for example, the user straightens up) the vehicle returns to its initial direction (the same direction as the body). This occurs because the body does not turn in this action and the vehicle rotation is relative to the body. If, on the other hand, the user does turn his head (looking into the turn) along with steering to one side, the behavior of the vehicle is to follow an arc as the body rotates, for instance a curve in the road. At the end of the maneuver, the vehicle and body will be facing a new, different direction.

Figure 5E:
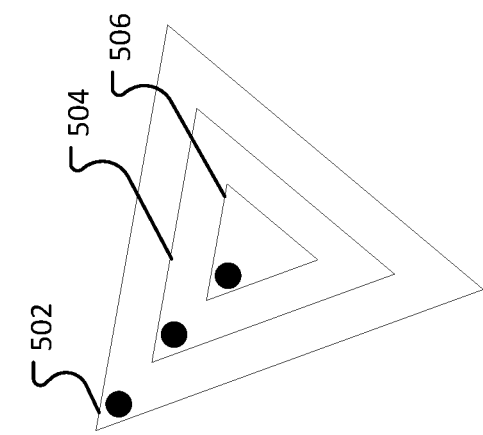

FIG. 5A-E illustrate examples of the responses of the vehicle and body to a steering input and an angle of head rotation. As described above, the angle of the head is determined based on the angle of virtual reality headset worn by the user, and consequently, by the angle of the user's actual head. Referring to FIG. 5A, three triangles represent the vehicle 502, the body or reference view point 504, and the head 506. The black dots represent the "front" of the vehicle 502, body 504, and head 506. In this figure, the vehicle 502, body 504, and head 506 are aligned. The positional velocity of the user's perspective is in the direction indicated by the vehicle 502. No rotational velocity is associated with either the vehicle 502, the body 504, or the head 506.

Referring to FIG. 5B, at some time after the time described by FIG. 5A, the system receives a steering input 508. The system checks to see if the head 506 has turned in the direction of the steering input 508. In this example, the head 506 has not rotated in the direction of the turn. A rotational velocity is applied to the vehicle 502, but no rotational velocity is applied to the body 504. The size of the rotational velocity of the vehicle can be determined based on the steering input 508.

In some implementations, the amount that the vehicle is turned is proportional to the steering input, and capped at 30 degrees from the angle of the body or reference view point. In other implementations, the vehicle rotation may be continuously driven using the steering input to determine the rotational velocity of the vehicle. As described above, positional velocity of the user's perspective is in the direction indicated by the vehicle 502.

Referring to FIG. 5C, the steering input 508 continues to be applied, but now the angle of the head 506 is in the direction of the turn. Based on the steering input 508 and angle of the head 506 the system applies a rotational velocity to the body 504, causing the body to turn in the direction of the steering input 508. In some implementations, the rotation of the body 504 may lag behind the rotation of the vehicle 506.

Figure 5D:
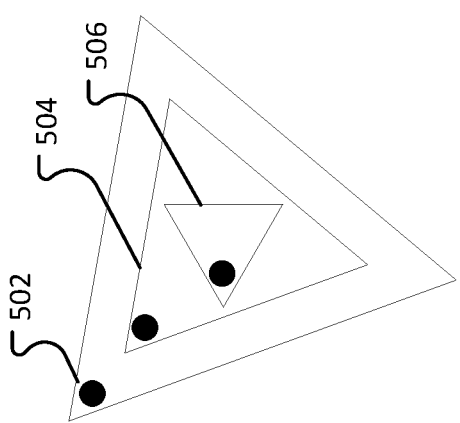

Referring to FIG. 5D, the steering input has been removed. The body 504 has moved into alignment with the vehicle 502. Without a steering input, the head 506 is free to rotate without causing a rotational velocity to be applied to the body 504. That is, the user may look around without causing the body to turn.

Referring to FIG. 5E, the vehicle 502, body 504, and head 506 are in alignment, and no steering input is being applied. The positional velocity of the user is in the direction indicated by the vehicle 502.

The system can also enforce a non-holonomic constraint, requiring that the user have some velocity in order to effectuate a turn. This may be used, for example, to prevent the sensation of "turning on a dime." Similarly, the system may limit the effect of the steering input a high virtual speeds. For example, a steering input at a slow speed may have a greater effect than a steering input at a high speed. This may be used, for example, to prevent the sensation of turning out of control. In some implementations, the system may increase the amount of a turn caused the steering input up to a speed threshold and then decrease the amount of turn caused by the steering input thereafter.

The data from the speed sensors is provided as input to determine the velocity the user traverses through the virtual environment. The velocity can be adjusted based on the virtual terrain. For example, the system may also alter the velocity of the user through the environment based on the apparent slope. For example, a user may be slowed down when traveling uphill, forcing the user to pedal faster to maintain the same apparent speed, while similarly the user may be sped up when traveling downhill. Below is an example of pseudo-code to control speed along the axial slope (the forward/back plane of the user direction) (e.g. travelling up or down a virtual hill):

```
if (sloping up)
{
    speed = speed * the minimum of 1 + 0.5 * the downward
    angle in radians, and
    1.5
}
else
{
    speed = speed * the maximum of 1 + 1.414 * the upward
    angle in radians, and
    0.1
}
```

As shown above, the adjustments to the user's speed may be asymmetric. For example, a user may be slowed down going uphill more than they speed up going downhill. In some implementations, the downhill speed is capped at one and a half times the regular speed.

In order to reduce the likelihood that a user suffers from simulation sickness, the system can limit the maximum angle of decent. For example, the system may limit the velocity vector to no more than forty-five degrees upward or downward.

Some virtual reality experiences may include simulating flight. For example, receiving data from a speed sensor which indicates that the user is moving with a predetermined speed can cause a vehicle to "fly". That is, the perspective of the user will leave the ground and travel upward. If the user slows down, the perspective of the user may return to the ground (land), however, the experience of going down and landing can be unpleasant for the user. Their visual senses tell them to expect a jolt, which does not come, or the user mentally supplies the jolt. In order to reduce the discomfort of the user, the system may smooth out the landing to minimize the sensation of impact.

When a user descends toward a virtual ground, either as a landing operation or as part of a free fall, the system may adjust the slope of the descent and ascent to reduce the sensation of impact. The user's descent may be adjusted to provide for a smooth landing. The user's descent may also be adjusted to provide a small impact. For example, in some implementations, the system is configured to establish the landing trajectory as smooth landing if the ground were 0.5 meters below the actual ground. This provides the user of the virtual reality system with a slight impact that is not overly disconcerting. An example of the pseudo-code to perform these operations is provided below:

```
if (the user is 10 virtual meters in the air)
{
    velocityDot = The dot product of a normal to ground
    vector and the velocity
vector;
        float minimum vertical speed = -velocityDot *
        currentVelocity.magnitude -
    Player Preference Factor * (hit.distance - threshold);
        if (minVertSpeed > ActivityProfile.LiftSpeed)
            minVertSpeed = ActivityProfile.LiftSpeed;
        if (currentVelocity.y < minVertSpeed)
            currentVelocity.y = minVertSpeed;
    }
}
```

The system also adjusts the terminal vertical velocity of the simulation. For example, the terminal velocity may be determined to be 3 virtual meters/second in a downward direction.

The system can also adjust velocity when the user is traveling along a transverse slope, (e.g. travelling across a hill). For example, the user may be slowed down proportional to the slope of the hill. Below is an example of pseudo-code to control speed along the transverse slope:

speed=speed*the maximum of 0.01 and 1.0–0.5*absolute value of the dot product of the vector to the ground and the vector describing the transverse slope.

A physics engine, or other system, may require a change to the velocity of the virtual vehicle, for example in response to a collision. The vehicle may be rotated to head in the direction of the new velocity. In order to reduce the likelihood of simulation sickness, the system may maintain a constant body rotation (which represents the reference view point) despite the rotation of the vehicle. After the collision, the vehicle's rotation and velocity may restored to correspond with the body rotation.

Figure 6:
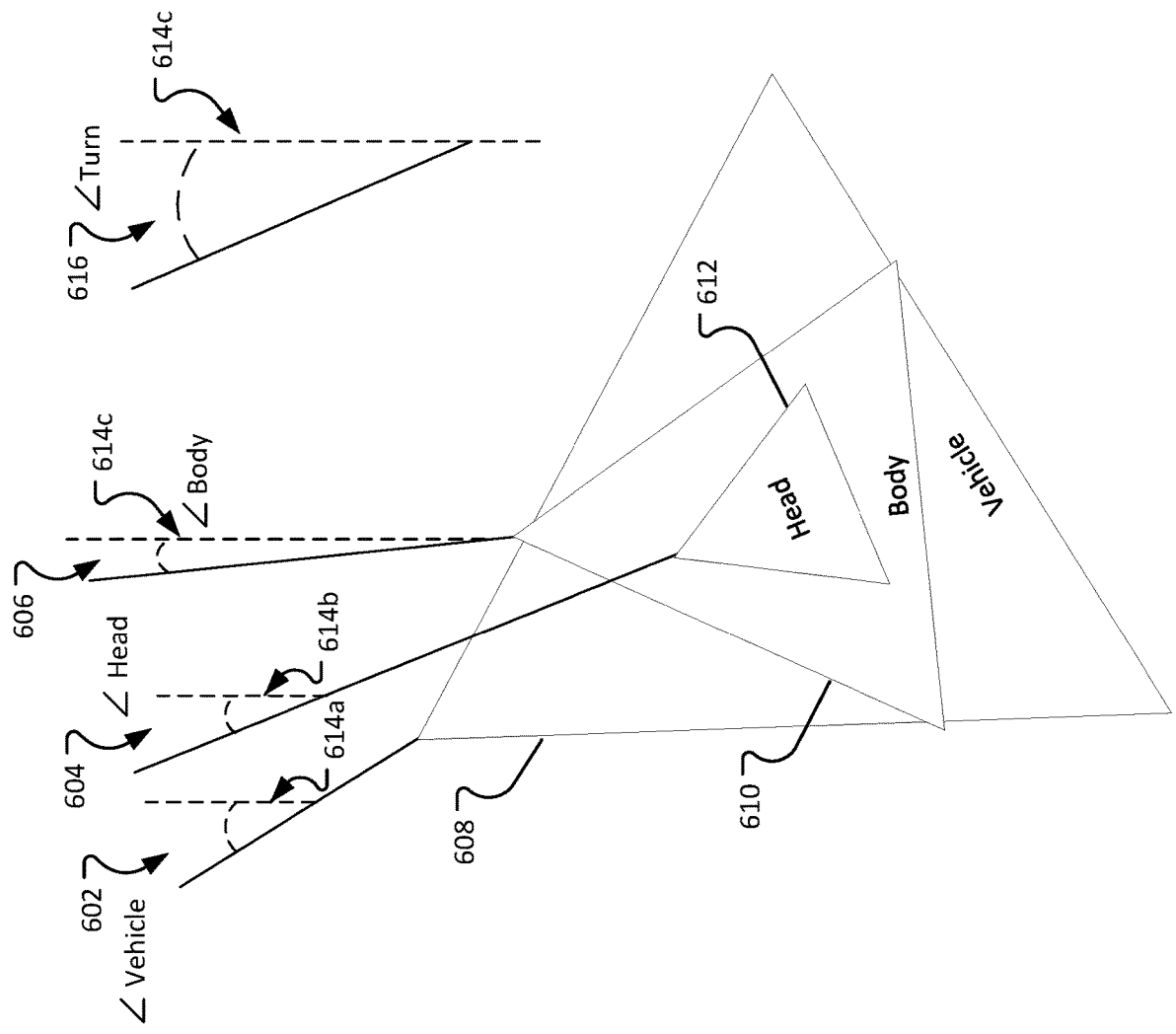
FIG. 6 illustrates an example relationship between a vehicle, a body, and a head.

FIG. 6 illustrates an example relationship between a vehicle 608, a body 610, and a head 612. As described above, the body 610 may or may not be represented by the virtual reality environment. In some implementations, the body is a reference rotation vector that indicates a direction the user looks when the user's actual head is in a default or resting position.

The vehicle 608 is oriented at an angle relative to a reference direction (represented by the parallel dotted lines 614a, 614b, 614c), represented by angle 602. The angle of the body 610 relative to the reference direction is represented by the angle 606. The angle of the head 612 is represented by angle 604. A steering input can be represented by the angle 616. The steering input drives the turning of vehicle 608 with respect to the body 610 as described above.

In some implementations, the rotational velocity of the body is proportional to the angle 604 of the head minus the angle of the body when the angle 604 of the head is between the angle 606 and the angle of the vehicle 602 (e.g., the angle of the vehicle 602 is greater than the angle 604 of the head and the angle 604 of the head is greater than the angle of the body 606).

In some implementations, the rotational velocity of the body is proportional to the angle 616 of the steering input when the angle 604 of the head is greater than the angle 602 of the vehicle.

In some implementations, the rotational velocity of the body is 0 when the angle 606 of the body is greater than the angle 604 of the head.

Other controls within the virtual reality environment may depend on the data from the steering sensor, speed sensors, and head sensor. For example, a virtual tank turret may follow the track the direction of the user's head, so that the turret moves to be line with the user's gaze.

Figure 7:
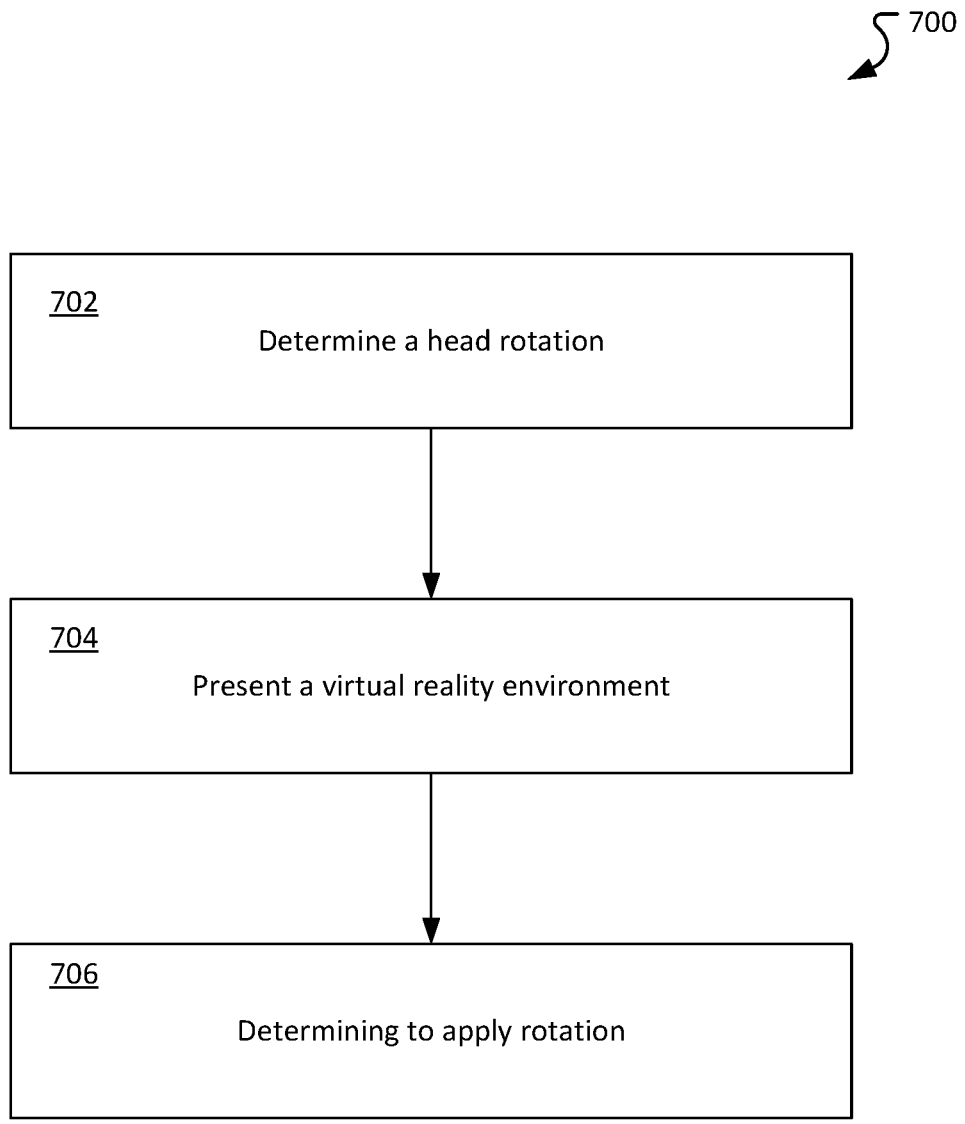
FIG. 7 is a flow chart of an example of a process for controlling a virtual reality exercise game.

FIG. 7 is a flow chart of an example of a process 700 for controlling a virtual reality exercise game. The process can be performed using a virtual reality exercise system, such as the virtual reality exercise system of FIG. 1 and FIG. 2.

The process 700 determines 702 a head rotation of a user and a head lean of the user on an exercise device. The head rotation can be based on data from one or more sensors.

The process 700 presents 704 a virtual reality environment on a virtual reality headset, where the perspective of the user in the virtual world is determined by a vehicle that defines the velocity of the perspective, a body which defines a reference view point of the perspective (with the head looking forward), and a head which defines the view point of the perspective.

The process 700 determines 706 to apply rotation to the body in response to determining that a direction of the head rotation is in a direction of the lean.

System Embodiment

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, a computer, a system on a chip, or multiple ones, or combinations, of the foregoing The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive, data from or transfer data to, or both, one or more mass storage devices for storing data (e.g., magnetic, magneto-optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system comprising:
    a virtual reality headset that has a forward-facing direction in a virtual world when a user wearing the virtual reality headset on a head of the user while seated on a stationary bike is looking forward;
    a sensor for receiving steering input from the user, including a position change or movement of the virtual reality headset being worn by the user seated position on the stationary bike;
    one or more processors configured to perform operations comprising:
        receiving speed data from the stationary bike;
        receiving steering data from the sensor indicative of a steering direction deviation from the forward-facing direction; and
        synchronizing vestibular and visual senses of the user by determining a magnitude of turning the forward-facing direction responsive to receiving the steering data and responsive to the position change or movement of the virtual reality headset;

wherein the position change comprises a lean of the head from an upright position, wherein a right lean is indicative of a right turn and wherein a left lean is indicative of a left turn; and wherein the right lean causes the right turn when the head of the user leans more than a threshold distance to a right side direction, and wherein the left lean causes the left turn when the head of the user leans more than the threshold distance to a left side direction.

2. The system of claim 1, wherein receiving the speed data while the forward-facing direction is being turned produces a curve-following motion, and the turning of the forward-facing direction is limited as a function of the speed data.

3. The system of claim 2, wherein the operations further comprise:
preventing, based on the function of the speed data, the turning of the forward-facing direction when a speed value of the speed data is zero; and
reducing the turning of the forward-facing direction when the speed value exceeds a threshold value.

4. The system of claim 1, wherein the steering input indicates a same direction as the lean of the head of the user, and wherein a direction and a magnitude of a turn are based on the lean of the head of the user when the lean has a larger turning value, and wherein the direction and the magnitude of the turn are based on the steering input when the steering input has the larger turning value.

5. The system of claim 1, wherein the steering input indicates a different direction than the lean of the head of the user, and wherein a direction and a magnitude of a turn are based on a combination of a first steering value from the lean of the head of the user and a second steering value from the steering input.

6. The system of claim 1, wherein the position change includes a rotation of the virtual reality headset, wherein the operations further comprise:
turning the forward-facing direction in response to the lean of the head and a rotation of the head of the user.

7. The system of claim 6, wherein the forward-facing direction follows an arc as the head of the user rotates and leans.

8. The system of claim 1, wherein the operations further comprise:
determining that the magnitude of the turning is zero when the steering input indicates a turn and the position change indicates that the user is not looking into the turn.

9. A virtual reality headset device comprising:
a frame wearable on a head of user, the frame supports one or more sensors configured to measure position changes of the head of the user relative to a forward-facing direction in a virtual world; and
one or more processors configured to perform operations including:
receiving motion data, from the one or more sensors, indicative of a change of the position or movement of a head of the user;
receiving a speed data from a stationary bike; and
synchronizing vestibular and visual senses of the user by determining a magnitude of moving the forward-facing direction in the virtual world responsive the speed data and responsive to the motion data indicative of a change of the position or movement of the head of the user;
wherein the change of the position of the head of the user comprises a lean of the head from an upright position of the user, wherein a right lean is indicative of a right turn and wherein a left lean is indicative of a left turn; and
wherein the right lean causes the right turn when the head of the user leans more than a threshold distance to a right side direction, and wherein the left lean causes the left turn when the head of the user leans more than the threshold distance to a left side direction.

10. The device of claim 9, wherein receiving the speed data while the forward-facing direction is being moved produces a curve-following motion, and the moving of the forward-facing direction is limited as a function of the speed data.

11. The device of claim 10, wherein the operations further comprise:
preventing, based on the function of the speed data, movement of the forward-facing direction when a speed value of the speed data is zero; and
reducing the movement of the forward-facing direction when the speed value exceeds a threshold value.

12. The device of claim 9, wherein a steering input indicates a same direction as the lean of the head of the user, and wherein a direction and a magnitude of a turn are based on the lean of the head of the user when the lean has a larger turning value, and wherein the direction and the magnitude of the turn are based on the steering input when the steering input has the larger turning value.

13. The device of claim 9, wherein a steering input indicates a different direction than the lean of the head of the user, and wherein a direction and a magnitude of a turn are based on a combination of a first steering value from the lean of the head of the user and a second steering value from the steering input.

14. The device of claim 9, wherein the change of the position of the head of the user further includes a rotation of the head of the user, wherein the operations further comprise:
turning the forward-facing direction in response to the lean of the head and the rotation of the head of the user.

15. The device of claim 14, wherein the forward-facing direction follows an arc as the head of the user rotates and leans.

16. One or more non-transitory computer readable media storing instructions that, when executed by one or more processors, are configured to cause the one or more processors to perform operations comprising:
receiving motion data, from one or more sensors, indicative of a change of a position or movement of a head of a user, the position being with respect to a forward-facing direction in a virtual world;
receiving a speed input from a stationary bike; and
synchronizing vestibular and visual senses of the user by determining a magnitude of moving the forward-facing direction in the virtual world responsive the speed input and responsive to the change of the position or movement of the head of the user;
wherein the change of the position of the head of the user comprises a lean of the head from an upright position of the user, wherein a right lean is indicative of a right turn and wherein a left lean is indicative of a left turn; and
wherein the right lean causes the right turn when the head of the user leans more than a threshold distance to a right side direction, and wherein the left lean causes the left turn when the head of the user leans more than the threshold distance to a left side direction.

* * * * *